US010881997B2

(12) United States Patent
Turbett et al.

(10) Patent No.: US 10,881,997 B2
(45) Date of Patent: Jan. 5, 2021

(54) METHOD OF STERILIZATION VERIFICATION

(71) Applicant: Turbett Surgical, Inc., Rochester, NY (US)

(72) Inventors: Robert E. Turbett, Penfield, NY (US); Richard D. Richmond, Canandaigua, NY (US)

(73) Assignee: Turbett Surgical, Inc., Rochester, NY (US)

( * ) Notice: Subject to any disclaimer, the term of this patent is extended or adjusted under 35 U.S.C. 154(b) by 101 days.

(21) Appl. No.: 16/108,343

(22) Filed: Aug. 22, 2018

(65) Prior Publication Data

US 2018/0353889 A1    Dec. 13, 2018

Related U.S. Application Data

(63) Continuation-in-part of application No. 15/461,895, filed on Mar. 17, 2017, now Pat. No. 10,226,728,
(Continued)

(51) Int. Cl.
*A61L 2/08* (2006.01)
*B01D 50/00* (2006.01)
(Continued)

(52) U.S. Cl.
CPC ............ *B01D 46/0005* (2013.01); *A61L 2/07* (2013.01); *A61L 2/28* (2013.01); *B01D 46/0002* (2013.01);
(Continued)

(58) Field of Classification Search
CPC ....... A61L 2/07; A61L 2202/24; B01D 25/02; B01D 29/54; B01D 46/002; B01D 46/0023
(Continued)

(56) References Cited

U.S. PATENT DOCUMENTS 2,981,196 A    4/1961  Zimmermann et al.
3,347,619 A   10/1967  Vischer
(Continued)

FOREIGN PATENT DOCUMENTS

AU    2006200911 B2    3/2007
CA       2759434 A1   11/2010
(Continued)

OTHER PUBLICATIONS

European Patent Office (EPO), European Search Report for corresponding EP Appl. No. 15743752.6-1370, dated Nov. 24, 2017.
(Continued)

*Primary Examiner* — Monzer R Chorbaji
(74) *Attorney, Agent, or Firm* — Jodi A. Reynolds, Esq.; Harter Secrest & Emery LLP

(57) ABSTRACT

A method of verifying sterilization comprises performing a sterilization cycle on a sterilizing cabinet, opening the door with the first filter overlying the vent port by a single user being non-sterile and ungowned and examining the first filter, by the single user being non-sterile and ungowned, to verify the integrity of the sterilization cycle in the sterilizing device, determining if the integrity of the first filter is acceptable by the single user being non-sterile and ungowned, and removing, by the single user being sterile and gowned, through the access port at least one tray from the interior of the sterilizing cabinet if the integrity of the first filter is acceptable.

19 Claims, 10 Drawing Sheets

Related U.S. Application Data which is a continuation of application No. 14/584,751, filed on Dec. 29, 2014, now Pat. No. 9,616,368, which is a continuation-in-part of application No. 14/167,691, filed on Jan. 29, 2014, now Pat. No. 10,245,335.

(51) Int. Cl.
  B01D 46/00 (2006.01)
  A61L 2/07 (2006.01)
  B01D 46/10 (2006.01)
  A61L 2/28 (2006.01)

(52) U.S. Cl.
  CPC ..... *B01D 46/0023* (2013.01); *B01D 46/0024* (2013.01); *B01D 46/10* (2013.01); *A61L 2202/121* (2013.01); *A61L 2202/122* (2013.01); *A61L 2202/15* (2013.01); *A61L 2202/24* (2013.01); *B01D 2279/35* (2013.01); *Y10T 29/49826* (2015.01)

(58) Field of Classification Search
  USPC ............ 422/26, 292, 295, 298, 300; 55/315; 96/108, 136
  See application file for complete search history.

(56) References Cited

U.S. PATENT DOCUMENTS

| | | |
|---|---|---|
| 3,351,422 A | 11/1967 | Jones et al. |
| 3,905,662 A | 9/1975 | Richmond |
| 3,925,043 A | 12/1975 | Matrone |
| 4,643,303 A | 2/1987 | Arp et al. |
| 4,661,326 A | 4/1987 | Schainholz |
| 4,670,227 A | 6/1987 | Smith |
| 4,671,943 A | 6/1987 | Inahlquist |
| 4,728,504 A | 3/1988 | Nichols |
| 4,997,240 A | 3/1991 | Schmalzl et al. |
| 5,072,960 A | 12/1991 | Sperko |
| 5,205,627 A | 4/1993 | Davison et al. |
| 5,224,812 A | 7/1993 | Oslin et al. |
| 5,324,489 A | 6/1994 | Nichols et al. |
| 5,346,075 A | 9/1994 | Nichols et al. |
| 5,352,416 A | 10/1994 | Wagner |
| 5,369,892 A | 12/1994 | Dhaemers |
| 5,417,729 A | 5/1995 | Greenleaf, Sr. |
| 5,553,986 A | 9/1996 | Napierkowski et al. |
| 5,732,821 A | 3/1998 | Stone et al. |
| 5,843,388 A | 12/1998 | Arroyo et al. |
| 5,893,618 A | 4/1999 | LePage, Jr. et al. |
| 5,968,459 A | 10/1999 | Nalepa et al. |
| 6,196,303 B1 | 3/2001 | Hepper |
| 6,572,819 B1 | 6/2003 | Wu et al. |
| 6,620,390 B1 | 9/2003 | Wagner |
| 6,789,815 B2 | 9/2004 | Moss et al. |
| 6,867,393 B1 | 3/2005 | Lewis |
| 7,455,067 B1 | 11/2008 | Cotton |
| 8,454,901 B1 | 6/2013 | Snyder, III |
| 8,505,959 B2 | 8/2013 | Darling, III |
| 9,439,992 B2 | 9/2016 | Webb et al. |
| 2002/0064478 A1 | 5/2002 | Davis |
| 2004/0001783 A1 | 1/2004 | Bowen |
| 2004/0011689 A1 | 1/2004 | Bauer |
| 2004/0062693 A1 | 4/2004 | Lin et al. |
| 2004/0090028 A1 | 5/2004 | Trogstam |
| 2004/0178137 A1 | 9/2004 | Itoh et al. |
| 2004/0256270 A1 | 12/2004 | Gleichauf et al. |
| 2005/0000553 A1 | 1/2005 | Noguchi et al. |
| 2005/0238530 A1 | 10/2005 | Frieze et al. |
| 2007/0039294 A1 | 2/2007 | Airey |
| 2008/0104990 A1 | 5/2008 | Lee et al. |
| 2009/0223972 A1 | 9/2009 | Allen |
| 2009/0272859 A1 | 11/2009 | Pippin |
| 2010/0166603 A1 | 7/2010 | Opie |
| 2011/0108554 A1 | 5/2011 | Ladison et al. |
| 2011/0114522 A1 | 5/2011 | Alston et al. |
| 2011/0308210 A1 | 12/2011 | Crabtree et al. |
| 2012/0082589 A1 | 4/2012 | Ladison et al. |
| 2012/0174922 A1 | 7/2012 | Virr et al. |
| 2013/0313029 A1 | 11/2013 | Franco |
| 2013/0322004 A1 | 12/2013 | Park |
| 2014/0348722 A1 | 11/2014 | Gray-Dreizler et al. |
| 2015/0023839 A1 | 1/2015 | Snyder et al. |
| 2015/0107627 A1 | 4/2015 | Snyder et al. |
| 2015/0231012 A1 | 8/2015 | Rapoport |
| 2015/0284018 A1 | 10/2015 | Krosney |
| 2015/0314026 A1 | 11/2015 | Mauzerall et al. |
| 2016/0008503 A1 | 1/2016 | Webb et al. |
| 2016/0346415 A1 | 12/2016 | Webb et al. |

FOREIGN PATENT DOCUMENTS

| | | | |
|---|---|---|---|
| CN | 1455684 A | 11/2003 | |
| CN | 1799632 A | 7/2006 | |
| CN | 201200633 Y | 3/2009 | |
| DE | 202004002095 U1 | 4/2004 | |
| DE | 202008001263 U1 | 7/2008 | |
| EP | 0077831 B1 | 9/1986 | |
| EP | 1905343 A1 | 4/2008 | |
| EP | 2737870 A2 | 6/2014 | |
| FR | 2986147 A1 | 8/2013 | |
| GB | 272284 | 6/1927 | |
| JP | S63-146647 | 6/1988 | |
| JP | H10-211262 | 8/1998 | |
| JP | H11-276559 | 10/1999 | |
| JP | 2001520552 | 10/2001 | |
| JP | 2002502668 | 1/2002 | |
| JP | 2007061596 | 3/2007 | |
| JP | 4189453 B2 | 12/2008 | |
| JP | 2009285009 A | 12/2009 | |
| JP | 2010-246847 | 11/2010 | |
| WO | 9847545 A3 | 10/1998 | |
| WO | 9940948 | 8/1999 | |
| WO | 2007000639 A1 | 1/2007 | |
| WO | 2007045943 A1 | 4/2007 | |
| WO | 2008061137 A2 | 5/2008 | |
| WO | 2010128408 A4 | 11/2010 | |
| WO | WO-2010128408 A1 * | 11/2010 | ............ A61B 50/13 |
| WO | 2012106506 A2 | 8/2012 | |
| WO | 2014159696 A1 | 10/2014 | |

OTHER PUBLICATIONS

European Patent Office (EPO), European Search Report for corresponding EP Appl. No. 15827680.8-1101, dated Jan. 31, 2018.
International Search Report and Written Opinion of the International Searching Authority in corresponding International Application No. PCT/US2015/010464; dated Apr. 3, 2015.
International Search Report and Written Opinion of the International Searching Authority in corresponding International Application No. PCT/US2016/025262; dated Jul. 5, 2016.
STERIS, "AMSCO Loading Car and Transfer Carriage—Type III", STERIS Corporation, pp. 1-2, Jul. 10, 1998, <www.steris.com>.
STERIS, "Loading Equipment for AMSCO Evolution and Evolution—L Steam Sterilizers—North America", STERIS Corporation, pp. 1-4, Feb. 1, 2011, <www.steris.com>.
STERIS, "AMSCO Sterilization Container System, Users Guide", STERIS Corporation, pp. 1-10, Apr. 2006, <www.steris.com>.
European Patent Office (EPO), Communication from EP Appl. No. 15743752.6 dated Sep. 29, 2016.
European Patent Office (EPO), Communication from EP Appl. No. 16774196.6 dated Nov. 17, 2017.
Japanese Patent Office (JPO), Office Action from JP Patent Appl. No. 2016-567331 dated Aug. 22, 2017.
Australia Govt., IP Australia, Office Action from AU Patent Appl. No. 2015211408 dated Jan. 12, 2017.
Canadian Intellectual Property Office (CIPO), Office Action from CA Patent Application No. 2,938,346 dated Apr. 18, 2017.
Aesculap Surgical Technologies SterilContainer System, archived on Jan. 24, 2013, accessed at hittp://web.archive.org/web/

(56) References Cited

OTHER PUBLICATIONS

20130124053037/http://www.aesculapusa.com/assets/base/doc/DOC132RevD-SterilContainerSystem.pdf.
European Patent Office (EPO), Extended European Search Report from EP Appl. No. 16774196.6 dated Aug. 24, 2018.
Chinese Patent Office (CPO), Office Action from CN Patent Application No. 201580015570.0 dated Jun. 5, 2019.
Japanese Patent Office (JPO), Office Action from JP Patent Application No. 2017-550718 dated Mar. 27, 2019.
Thempson, "Sterile Container System & Baskets", Thempson Surgical Instruments, pp. 1-48. Accessed at http://www.thempson.com/downloads.html.
European Patent Office, Office Action in corresponding EP Application No. 16774196.6, dated Feb. 6, 2020.
European Patent Office, Extended European Search Report in corresponding EP Application No. 19210878.5, dated Apr. 8, 2020.
European Patent Office, Office Action from corresponding EP Application No. 16774196.6, dated Oct. 7, 2020.
Indian Patent Office, First Examination Report from corresponding in Application No. 201617028262, dated Oct. 12, 2020.

\* cited by examiner

METHOD OF STERILIZATION VERIFICATION

CROSS-REFERENCE TO RELATED APPLICATIONS

The present application is a Continuation-In-Part of co-pending U.S. patent application Ser. No. 15/461,895 filed on Mar. 17, 2017 and incorporated herein by reference; application Ser. No. 15/461,895 is a Continuation application of U.S. patent application Ser. No. 14/584,751 filed on Dec. 29, 2014, now U.S. Pat. No. 9,616,368 and incorporated herein by reference, which in turn is a Continuation-In-Part of U.S. patent application Ser. No. 14/167,691 filed on Jan. 29, 2014, and incorporated herein by reference.

BACKGROUND OF THE INVENTION

Field of the Invention

Exemplary configurations of the present disclosure relate to a method for sterilization and more particularly to a method for verifying sterilization of a sterilization cabinet.

Description of Related Art

Sterilization is a term referring to any process that eliminates (removes) or kills microbial life, including transmissible agents (such as fungi, bacteria, viruses, or spore forms) present on a surface, or contained in a fluid, or in medication, or in a compound such as biological culture media. Sterilization can be achieved by applying heat, chemicals, irradiation, high pressure, and filtration or combinations thereof.

In general, surgical instruments, implants, and medications that enter an already aseptic part of the body (such as the bloodstream or penetrating the skin) must be sterilized to a high sterility assurance level. Examples of such instruments include scalpels, hypodermic needles and implantable medical devices (IMD), such as artificial pacemakers.

A widely used method for heat sterilization is the autoclave, sometimes referred to as a converter. Autoclaves commonly use steam heated to 121-134° C. To achieve a degree of sterility, a holding time of at least 15 minutes at 121° C. at 100 kPA, or 3 minutes at 134° C. at 100 kPa is required. Additional sterilizing time is usually required for liquids and instruments packed in layers of cloth, as they may take longer to reach the required temperature.

One method of sterilization involves passing steam through a cabinet. For effective sterilization, steam needs to penetrate the cabinet load uniformly. Accordingly, the cabinet must not be overcrowded, and the lids of bottles and containers must be left ajar. During the initial heating of the chamber, residual air must be removed. Indicators should be placed in the most difficult places for the steam to reach to ensure that steam actually penetrates there. A filter is typically placed over the vent to keep particles or extraneous materials from entering the cabinet before, during or after the sterilizing process.

To ensure sterilization is maintained after the sterilization cycle is complete, users follow comprehensive sterilization guidelines. For example, the Association for the Advancement of Medical Instrumentations (AAMI) for healthcare facilities recently established the *Comprehensive Guide to Steam Sterilization and Sterility Assurance in Health Care Facilities* (ANSI/AAMI ST79:2006) to provide guidelines on instrument sterilization. The ANSI/AAMI ST79:2006 includes five recommended practices: Steam sterilization and sterility assurance in health care facilities (ANSI/AAMI ST46); Steam sterilization and sterility assurance using table-top sterilizers in office-based, ambulatory-care medical, surgical, and dental facilities (ANSI/AAMI ST42); Flash Sterilization: Steam sterilization of patient care items for immediate use (ANSI/AAMI ST37); Safe handling and biological decontamination of medical devices in health care facilities and in nonclinical settings (ANSI/AAMI ST35); and Guidelines for the selection and use of reusable rigid sterilization container systems for ethylene oxide sterilization and steam sterilization in health care facilities (ANSI/AAMI ST33).

With respect to sterilizing cabinets, these guidelines require that the filter or filters of a sterilizing cabinet be inspected by a medical professional once the sterilizing process is completed to verify the integrity of the sterilizing process was maintained. If it is discovered during inspection that the filter did not remain intact, or is otherwise ripped, torn, wet, and/or punctured, the sterilizing process has to be repeated with a new filter.

A disadvantage of current sterilization verification methods is that the procedure of verifying sterilization typically requires two individuals to participate in the sterilization verification process because the contents of the sterilizing cabinet (which are sterile) must be removed to access the filter. For example, a first individual that has not yet followed guidelines for sterile gowning and gloving opens a door of a sterilizing cabinet, while a second individual, having followed guidelines for sterile gowning and gloving, removes the contents within the sterilization cabinet from the sterilization cabinet to a separate, sterile field. After the contents are removed, the first individual can now remove the filter from the sterilizing cabinet to a non-sterile field and perform a visual inspection to determine if the filter is torn, punctured, wet, or otherwise compromised. If the integrity of the filter is verified, the contents are deemed to be sterile and can be transported to the desired location. If the filter is deemed to be compromised, the filter is replaced with a new filter and the contents are placed back into the sterilization cabinet for another sterilization cycle to be performed.

Another disadvantage of the current sterilization verification methods is that the procedures typically require the contents of the sterilization cabinet to be removed so that the filter can be accessed for visual inspection.

Another disadvantage of the current sterilization verification methods is that the procedures require the preparation and use of a sterile field before sterilization of the contents can be verified.

What is needed, then, is a method that does not require more than one individual for verifying sterilization of contents in a sterilization cabinet.

Also needed, is a method for verifying the integrity of a filter before the contents are removed from the sterilization cabinet.

It would, therefore, be desirable to provide a method that overcomes the aforesaid and other disadvantages.

BRIEF SUMMARY OF THE INVENTION

A first exemplary configuration of the present disclosure provides a method for verifying sterilization. The method comprises performing a sterilization cycle on a sterilizing cabinet having an access port, an interior having at least one tray sized to retain a plurality of medical instruments, and a door having a vent port and a filter overlying the vent port, the door connected to the sterilizing cabinet and moveable between an open position and a closed position. The method further includes opening the door with the first filter overlying the vent port by a single user being non-sterile and ungowned and examining the first filter, by the single user being non-sterile and ungowned, to verify the integrity of the sterilization cycle in the sterilizing device. The method also includes determining if the integrity of the first filter is acceptable by the single user being non-sterile and ungowned. Further, the method includes removing, by the single user being sterile and gowned, through the access port at least one tray from the interior of the sterilizing cabinet if the integrity of the first filter is acceptable.

A second exemplary configuration of the present disclosure provides a method for verifying sterilization. The method comprises performing a sterilization cycle on a sterilizing cabinet, the sterilizing cabinet having an access port and a door connected to the sterilizing cabinet, the door having a vent port and a filter overlying the vent port, the door moveable between an open position permitting passage through the access port to an interior of the sterilizing cabinet having at least one tray sized to retain a plurality of medical instruments, and a closed position precluding passage though the access port. The method further includes removing the door having the filter overlying the vent port by a single user being non-sterile and ungowned. Also included in the method is the step of examining the filter, by the single user being non-sterile and ungowned, to verify the integrity of the sterilization cycle in the sterilizing device. The method further includes determining whether the integrity of the filter is acceptable by the single user being non-sterile and ungowned, and removing at least one tray from the interior of the sterilizing cabinet through the access port by the single user being sterile and gowned if the integrity of the first filter is acceptable.

The following will describe configurations of the present disclosure, but it should be appreciated that the present disclosure is not limited to the described configurations and various modifications of the invention are possible without departing from the basic principle. The scope of the present disclosure is therefore to be determined solely by the appended claims.

BRIEF DESCRIPTION OF THE SEVERAL VIEWS OF THE DRAWING(S)

DETAILED DESCRIPTION OF THE INVENTION

At the outset, it should be appreciated that like drawing numbers on different drawing views identify identical structural elements of the invention. While the present invention is described with respect to what is presently considered to be the preferred configuration, it is understood that the invention is not limited to the disclosed configuration.

Furthermore, it is understood that the invention is not limited to the particular methodology, materials, and modifications described and as such may vary. It is also understood that the terminology used herein is for the purpose of describing particular elements only, and is not intended to limit the scope of the present invention, which is limited only by the appended claims.

In the medical field, it is of the utmost importance that medical instruments are sterilized prior to any medical procedure. This drastically helps prevent the spread of infectious materials and reduces the risk of infection of a patient. Currently, there are a wide variety of devices that provide for sterilization of medical instruments, equipment and implants through the use of a sterilizing agent. A widely used method for heat sterilization using steam is an autoclave. Rigid containers, or sterilization cabinets containing instruments, equipment and/or implants to be sterilized, can be loaded into the autoclave, wherein steam will infiltrate the container during a sterilizing cycle to sterilize the contents.

Figure 1:
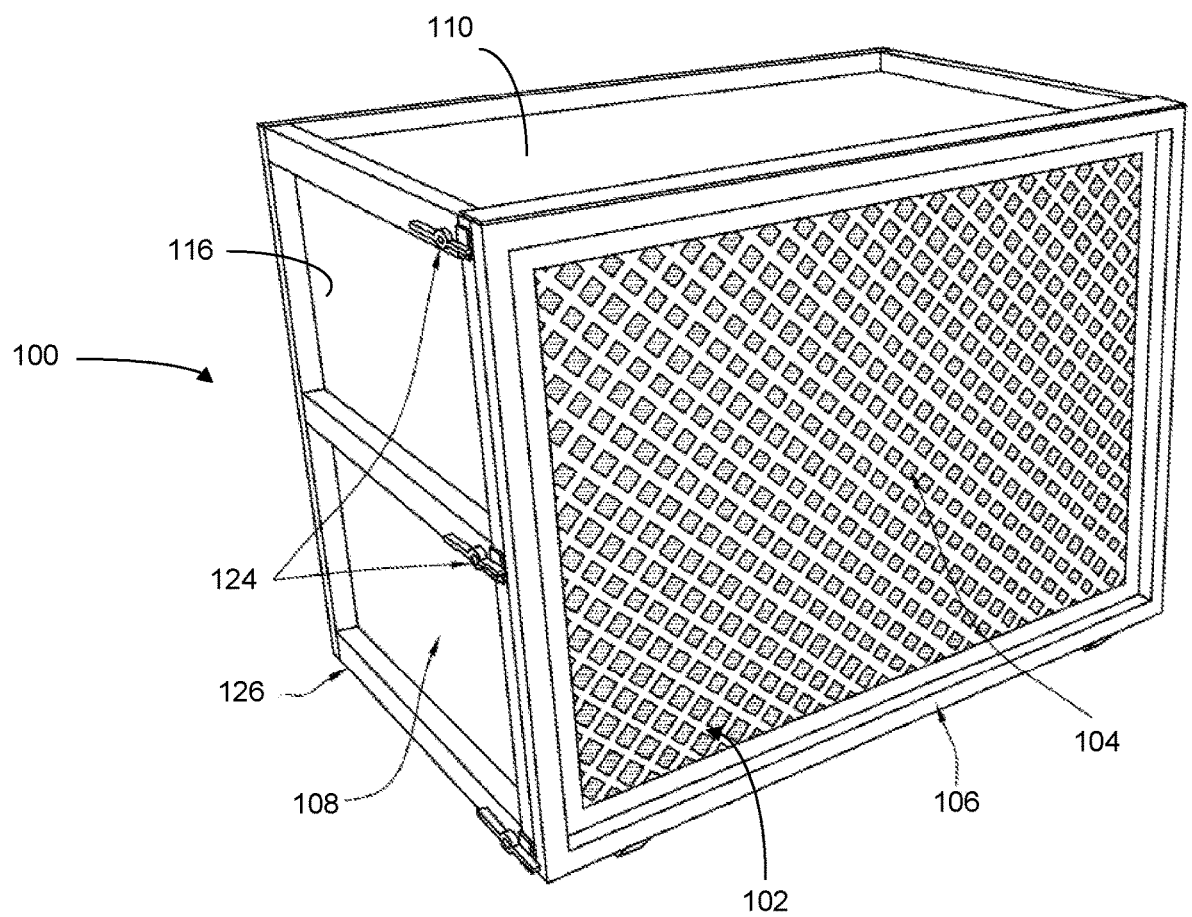
FIG. 1 is a perspective view of a configuration of a sterilizing cabinet suitable for use in practicing exemplary configurations of this invention.

Referring now to the Figures, FIG. 1 is a perspective view of one configuration of a sterilizing cabinet 100 that can be used to perform the methods of sterilization verification disclosed herein. The term sterilizing cabinet encompasses any device capable of sterilizing. The term also includes sterilizing cabinets for holding items to be sterilized in a sterilizer, including, but not limited to, medical instruments, surgical devices and the like.

The sterilizing cabinet 100 includes a vent 102 for venting the steam of a sterilizer used to sterilize the contents of the sterilizing cabinet 100. Typically, at least one filter 104 covers the vent 102. The filter 104 prevents extraneous materials from entering the sterilizing cabinet 100 during and after the sterilization cycle and allows sterilizing steam to enter and exit the sterilizing cabinet 100. The sterilizing cabinet 100 includes a door 106 and a body 108. The body 108 includes a top wall 110, bottom wall, two sidewalls 116, and a backwall (not shown) such that an access port and an interior of the sterilizing cabinet 100 are formed. In some configurations, the door 106 is removeable from the body 108. In other configurations, the door 106 can be opened, but is fixedly connected to the body 108. The sterling cabinet 100 may further include latch or latches 124 to attach the door 106 to the body 108. It should be appreciated that latches 124 can include any type of clamping, latching or clasping device known in the art that is able to releasable attach the door 106 to the body 108 such that a sealed interface is created between door 106 and sterilizing cabinet 100.

The door 106, in a configuration, includes the vent port 102. In an assembled position, a filter 104 overlies the vent port 102 of the door 106 such that when the door 106 is moved to a closed position to preclude passage through an access port, the filter 104 forms a sealed interface between confronting surfaces of the door 106 and the cabinet 100. The confronting surface of the door 106 and cabinet 100 should be dent-free and the door 106 should matingly engage the confronting surface of the sterilizing cabinet 100 to ensure a seal can be properly formed. In an open position, passage through the access port to an interior of the sterilizing cabinet 100 is permitted.

As illustrated, the body 108 of the sterilizing cabinet 100 is maintained within a frame 126. Frame 126 provides a structurally reinforcing frame for sterilizing cabinet 100 and may be made of any type of metal, plastic, composite, or aluminum alloy. Exemplary configurations of body 108 and frame 126 are able to repeatedly undergo sterilizing cycles (e.g., steam sterilizing cycles or other types of sterilizing cycles) and maintain their structural integrity.

Figure 2:
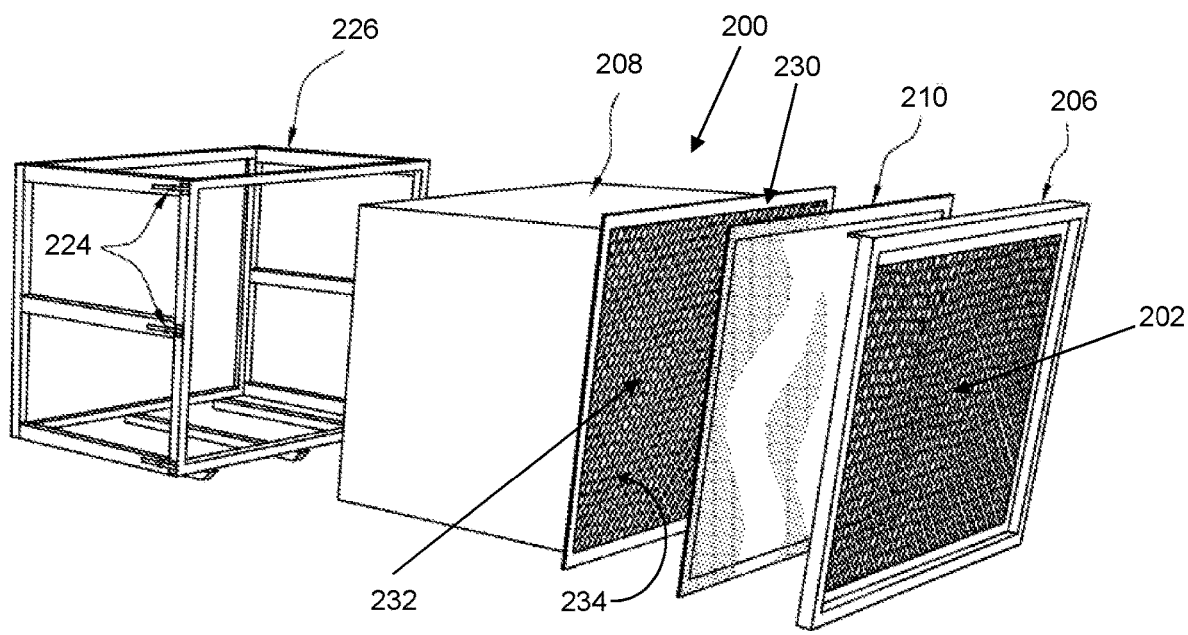
FIG. 2 is a perspective view of an alternative configuration of a sterilizing cabinet suitable for use in practicing exemplary configurations of this invention.

Referring to FIG. 2, shown is a perspective view of an alternative configuration of a sterilizing cabinet 200 suitable for use in practicing exemplary methods of this disclosure. Shown in FIG. 2 are sterilizing cabinet 200, vent 202, filter door 206, body 208, filter cartridge 210, and latches 224. In some configurations, as shown in FIG. 2, sterilizing cabinet 200 can be removed from frame 126 when filter door 206 is released from removable frame 226 by latches 224. In other exemplary configurations, frame 226 is not removable from sterilizing cabinet 200, but is fixedly attached to sterilizing cabinet 200. In yet another exemplary configuration, the sterilizing cabinet 200 does not include a frame 226. Filter door 206, as depicted, includes a fenestrated grid throughout its center. However, exemplary configurations of filter door 206 include any type of arrangement of holes, gaps, or grids such that sterilizing steam is free to pass through the center portion of filter door 206.

The sterilizing cabinet 200 can include a second filter door 230 and second filter 232 (the second filter 232 located between filter door 230 and body 208). In one configuration, the second filter door 230 having the second filter 232 is disposed between the body 208 of the sterilizing cabinet 200 and the filter 210. The second filter door 230 includes a vent port 234 such that, in an assembled position, the filter 232 overlies the vent port 234 of the door 230. Thus, during a sterilizing cycle, a first seal is maintained between the filter door 230 and the body 208 while a second seal is maintained between the filter door 206 and the filter door 230 or, if the second filter door 230 and filter 232 are recessed or co-planar, with the access port of the sterilizing cabinet 200 between the filter door 206 and a perimeter of the body 208.

In one configuration the sterilizing cabinet 200 includes one tray in the interior of the sterilizing cabinet. In another configuration, the sterilizing cabinet 200 includes a plurality of trays. Each tray may be sized to hold a plurality of instruments and/or devices needing to be sterilized. Typically, a tray includes a base and sidewalls. However, a tray having a base with no sidewalls, or a tray having a base with a perimeter edge having a rim or ledge is possible. In a configuration, the tray is loaded into the sterilizing cabinet 200 unwrapped. That is, the tray is not wrapped with filter paper or other type of sterilization barrier before being placed in the sterilizing cabinet 200.

Figure 3:
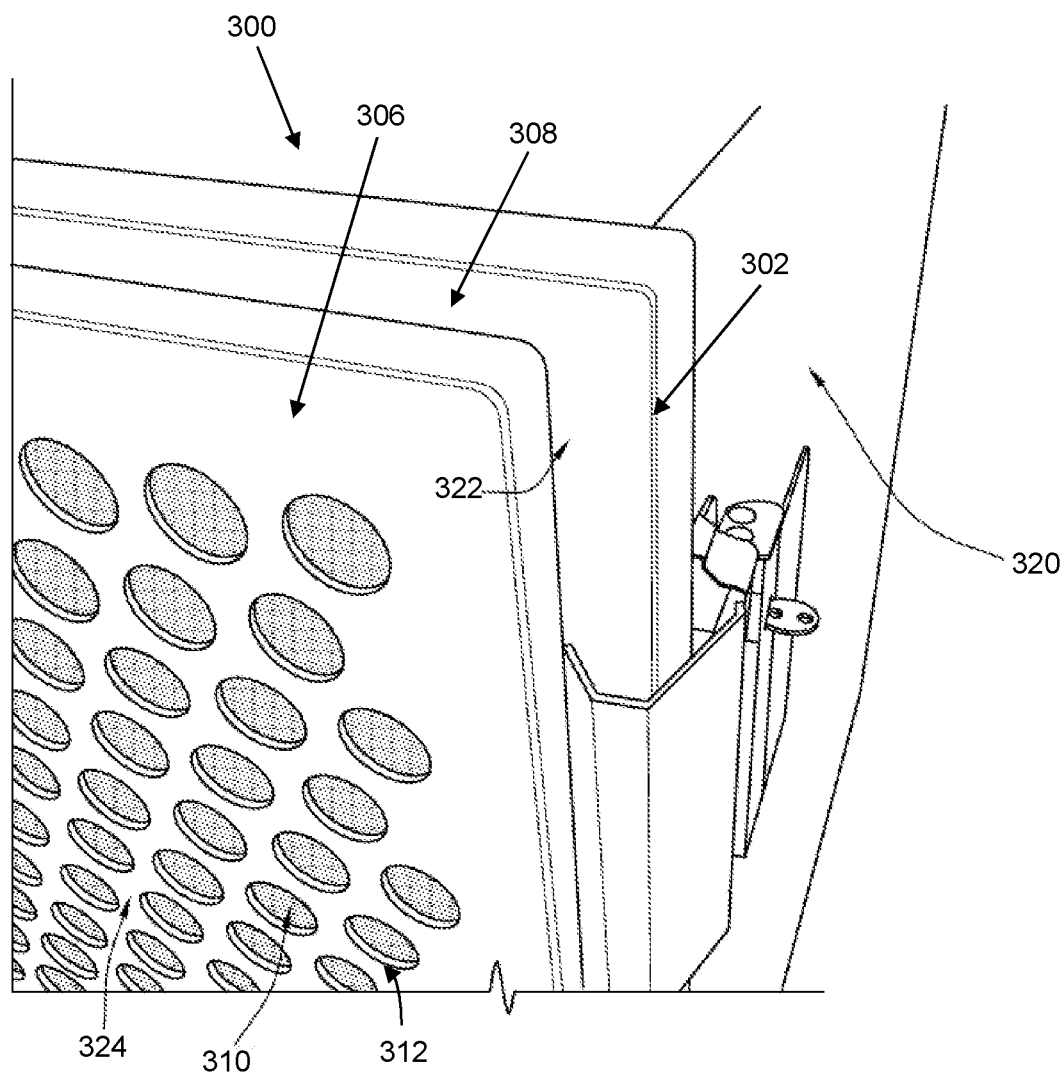
FIG. 3 is a perspective view of an configuration of a sterilizing cabinet suitable for use in practicing exemplary configurations of this disclosure.
Figure 4:
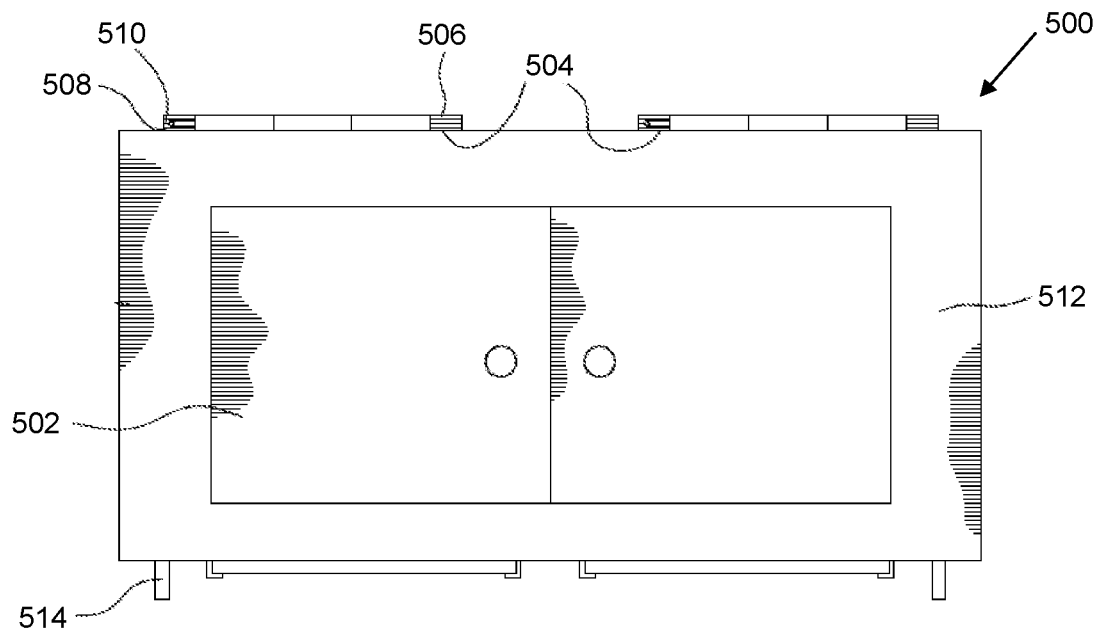
FIG. 4 is a front view of another configuration of a sterilizing cabinet suitable for use in practicing exemplary configurations of this invention.

As shown in FIG. 3, the sterilizing cabinet 300 includes an access port 302 such that when the door 306 is in an open position, passage through the access port 302 to an interior 308 of the sterilizing cabinet 300 is permitted. As shown in FIG. 3, in this configuration, door 306 includes vent port 312, wherein a filter 310 overlies the vent port 312. The door 306 includes a confronting surface for forming a sealed interface between the door 306 and the sterilizing cabinet 300.

The interface between the filters 104, 210, 232, and the sterilizing cabinet 100, 200, or 300 is effectively sealed either prior to or during or at the completion of the sterilization cycle. That is, at least before the autoclave is opened, a sealed interface is formed between the seal or seals of the filters 104, 210, and/or 232 and the sterilizing cabinet 100, 200, or 300. It is understood the seal of the filter 104, 210, and/or 232, and the sterilizing cabinet 100, 200, or 300 may go through a transformation during the sterilization cycle. When the filter 104, 210, and/or 232, is initially operably located relative to the sterilizing cabinet 100, 200, or 300, a seal can be formed. However, it is contemplated that the initial operable location of the seal relative to the sterilizing cabinet 100, 200, or 300 may not form a seal, wherein the sealed interface is formed during the sterilization cycle or at the completion of the sterilization cycle.

Figure 5:
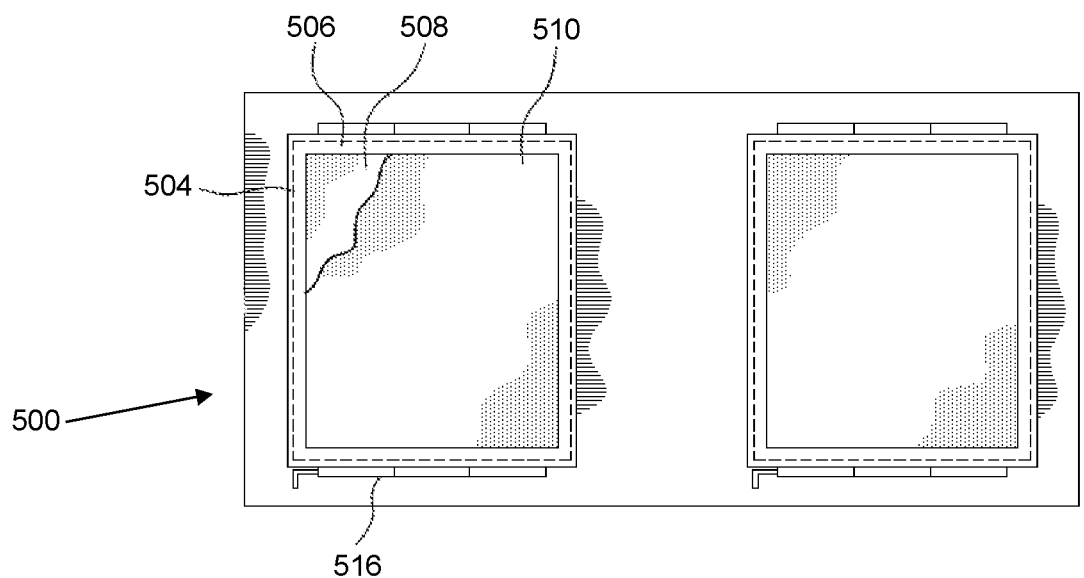
FIG. 5 is a top view of the configuration of the sterilizing cabinet of FIG. 4.

Referring to FIGS. 4-8, FIG. 4 is a front view of sterilizing cabinet 500 and FIG. 5 is a top view of sterilizing cabinet 500 that can be used to perform the methods of sterilization verification disclosed herein. It should be noted that configurations of the present methods are not limited to the particular configuration of sterilizing cabinet 100, 200, 300, or 500. Sterilizing cabinet 500 in this configuration, includes door or doors 502, vents 504, filter holder 550, primary filter 508, sterilizing cabinet frame 512 and legs 514. The sterilizing cabinet 500 may include secondary filter 510. Door or doors 502 are able to open and close for access to the interior of sterilizing cabinet 500. In the configuration shown, door or doors 502 are physically connected to sterilizing cabinet frame 512. Door or doors 502 can be attached through the use of a hinge or hinges which allows the doors to swing open. Alternatively, door or doors 502 can be removable from sterilizing cabinet 500 through the use of clamps (not shown in FIG. 4). It should be appreciated that exemplary configurations of door or doors 502 include any mechanism that allows for door or doors 502 to move from an open position to a closed position to provide access to the interior of sterilizing cabinet 500.

FIG. 5 further provides a top view of sterilizing cabinet 500 showing vent 504 covered by filter holder (or door) 550, primary filter 508, secondary filter 510, sterilizing cabinet frame 512 and hinge 516 of filter holder (or door) 554. Hinge 516 with filter holder 554 allows a portion of filter holder 554 to swing open about hinge 516 such that primary filter 508 and secondary filter 510 can be removed independent of one another. In other words, filter holder 554 allows for secondary filter 510 to be released and removed from filter holder 554 while simultaneously maintaining primary filter's 508 seal with sterilizing cabinet 500 over vent 504.

Figure 6:
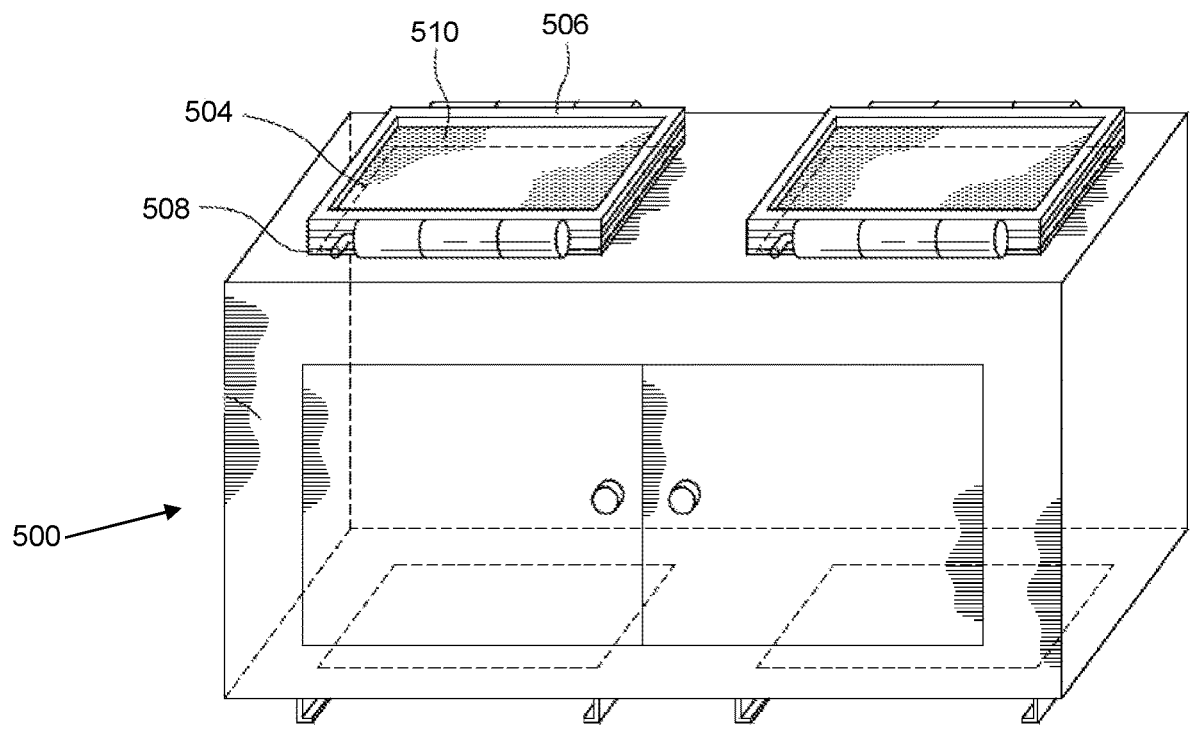
FIG. 6 is a perspective view of the configuration of the sterilizing cabinet of FIG. 4 showing an internal view of the sterilizing cabinet.

Sterilizing cabinet 500 in this configuration provides for four vents 504 as shown in FIG. 6. However, it should be appreciated that exemplary configurations of sterilizing cabinet 500 are not limited to four vents. Exemplary configurations of sterilizing cabinet 500 can include one or more vents. Two vents 504 on the top of sterilizing cabinet 500 and two vents 504 on the bottom of sterilizing cabinet 500. Vents 504 provide numerous small openings for the passage of sterilizing steam. The small openings in vents 504 can be holes or slits. Alternatively, vents 504 can be fenestrated.

Figure 7:
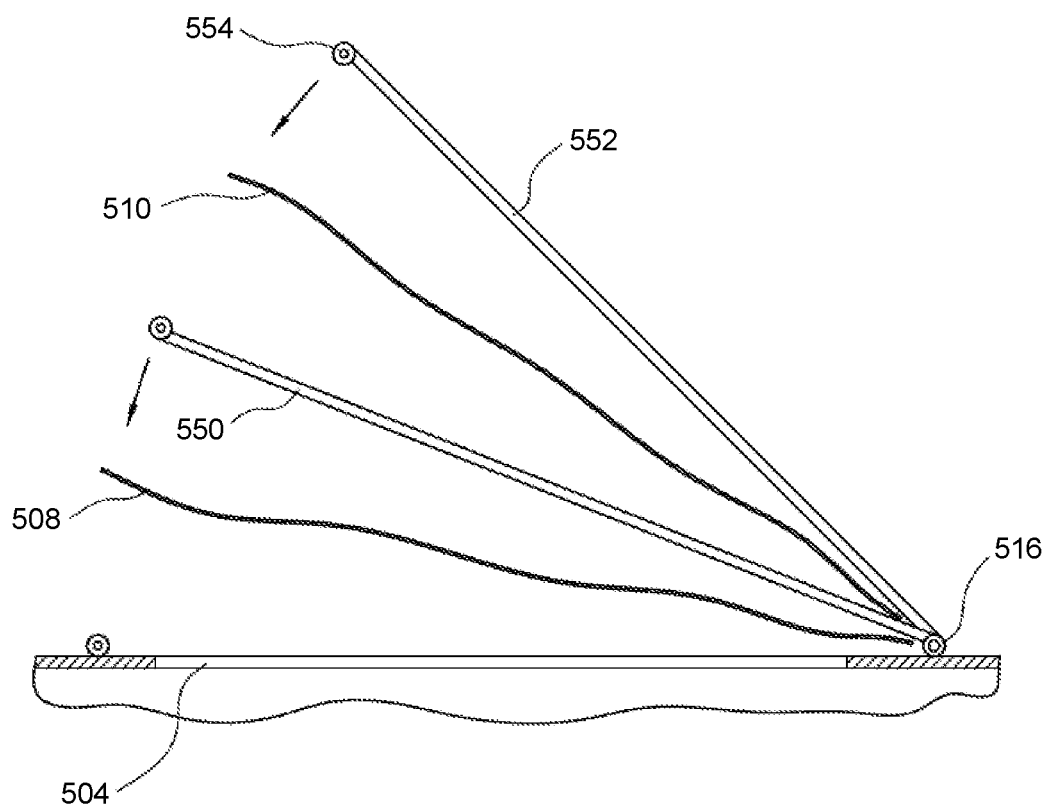
FIG. 7 is a side view of a filter arrangement of the sterilizing cabinet of FIG. 4 for use in practicing exemplary configurations of the invention.
Figure 8:
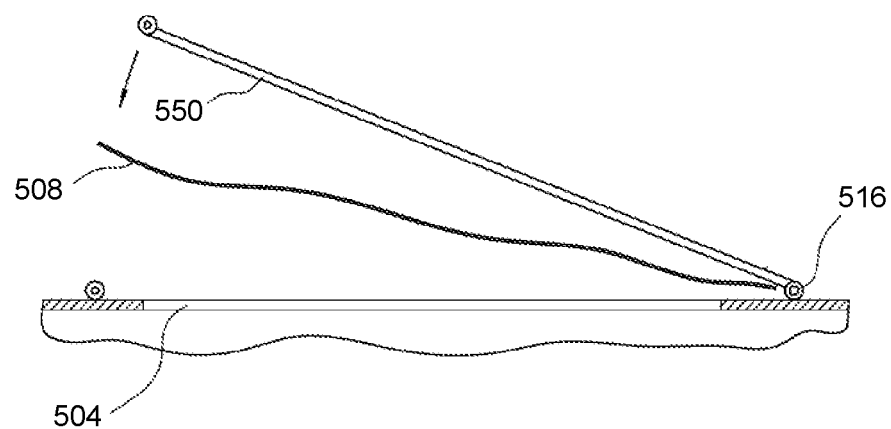
FIG. 8 is a side view of an alternative configuration of a filter arrangement of the sterilizing cabinet of FIG. 4 for use in practicing exemplary configurations of this invention.

As shown in FIGS. 7 and 8, primary filter 508 in conjunction with filter holder 550 covers vent 504. Primary filter 508 with filter holder 550 forms a seal with the adjacent portions of sterilizing cabinet 500 such that during the operation of a sterilizing cycle, any sterilizing steam that passes through the vent 504 must then pass through primary filter 508. Primary filter 508 can be made of a very thin paper. Exemplary configurations provide that primary filter 508 can be made of any porous material that (1) allows for the passage of sterilizing steam from sterilizing cabinet 500 and (2) prevents extraneous materials from passing through primary filter 508 and entering vent 504. Primary filter 508 may be configured as a filter cartridge as described supra. Primary filter 508 is removable from sterilizing cabinet 500 and is typically a single-use filter, and therefore, replaced with a new filter following each sterilizing cycle.

In a configuration, secondary filter 510 resides on top of primary filter 508 in filter holder 554. Secondary filter 510 covers primary filter 508 and forms a seal with primary filter 508 through filter holder 554 such that any sterilizing steam that passes through the vent 504 must then pass through primary filter 508 and secondary filter 510. Secondary filter 510 can be made of a very thin paper. Secondary filter 510 can be made of any porous material that (1) allows for the passage of sterilizing steam from sterilizing cabinet 400 and primary filter 408 and (2) prevents extraneous materials from passing through secondary filter 408. Secondary filter 510 may be configured as a filter cartridge as described supra.

Exemplary configurations of this disclosure provide for secondary filter 510 to form a sealed periphery with primary filter 508. In another exemplary configuration the sealed interface between the primary filter 508 and the adjacent portion of either the sterilizing cabinet 500 is independent of an interface between secondary filter 510 and primary filter 508. One exemplary arrangement provides for primary filter 508 and secondary filter 510 to be coextensive. In another exemplary configuration primary filter 508 and secondary filter 510 have different filter properties. For instance, primary filter 508 and secondary filter 510 may filter different elements of the sterilizing agent which exits sterilizing cabinet 500 during a sterilization cycle. In an alternative exemplary configuration primary filter 508 and secondary filter 510 have similar filter properties. Another exemplary configuration provides that primary filter 508 and secondary filter 510 are different colors.

In yet another exemplary configuration, as shown in FIG. 8, primary filter 508 may be the only filter that covers vent 504. Here, primary filter 508 is removeably held or maintained in place over vent 504 by filter holder 550. In this configuration, there is no secondary filter. Primary filter 508 forms a seal with the adjacent portions of sterilizing cabinet 500 such that during the operation of a sterilizing cycle, any sterilizing steam that passes through the vent 504 must then pass through primary filter 508. Again, in this configuration, primary filter 508 can be made of any porous material that (1) allows for the passage of sterilizing steam from sterilizing cabinet 500 and (2) prevents extraneous materials from passing through primary filter 508 and entering vent 504. Primary filter 508 is removable from sterilizing cabinet 500 and is typically replaced with a new filter following each sterilizing cycle.

Legs 514 reside on the bottom of sterilizing cabinet 500 and provide spacing between the surface which sterilizing cabinet 500 rests and the bottom primary filter 508, secondary filter 510 and filter holder 554.

In exemplary configurations sterilizing cabinet 500 may include a steam exposure indicator on either the primary filter 508 or the secondary filter 510 which designates when steam from sterilizing cabinet 500 has passed through one of the filters. An example of one such steam exposure indicator is a tape that changes colors when exposed to steam.

In practice, an exemplary configuration of a process of placing primary filter 508 and secondary filter 510 includes disposing primary filter 508 to occlude a vent 504 of sterilizing cabinet 500 and forming a first sealed interface with the sterilizing cabinet 500. The process continues by forming a second sealed interface between secondary filter 510 (or confirmatory filter) and at least a portion of one of sterilizing cabinet 500 and primary filter 508, a portion of the secondary filter 510 overlying a portion of the primary filter 508. The process can continue by passing a sterilizing agent (typically steam) through primary filter 508 and secondary filter 510 and vent 504.

Also in practice, an exemplary configuration of a process of placing only a primary filter 508 includes disposing primary filter 508 with filter holder 550 to occlude vent 504 of sterilizing cabinet 500 creating a sealed interface with the sterilizing cabinet 500. The process can continue by passing a sterilizing agent (typically steam) through primary filter 508 and vent 504. The process can then conclude with verifying the integrity of primary filter 508 by either inspecting primary filter 508 while it covers vent 504 in filter holder 550 or after it is removed from filter holder 550. The process may be repeated if it is determined that the integrity of primary filter 508 was compromised during the sterilizing process.

With respect to the seal, when exposed to the sterilization cycle, (in select cases, heat in the form of steam, and pressure) may undergo slight transformation of the seal configuration, and either become more form fitting to the sealing surface area or even result in seal formation. This change in the seal during the sterilization cycle may create a more robust seal than when it was originally placed. Thus, the interface between the filters and the sterilizing cabinet 100, 200, 300, or 500 can be dynamic, forming a seal during the sterilization cycle, or static, entering the sterilization cycle with the sealed interface and maintaining the sealed interface throughout the sterilization cycle. It is contemplated a variety of materials can be used to enhance or form a seal between the filter (or the cartridge) and the sterilizing cabinet, such as but not limited to card stocks, thermoplastics, thermoplastic elastomers, polymers and waxes.

It should be appreciated by those having ordinary skill in the art that the filter may take many different configurations. In one configuration, the filter is a cartridge having a frame and a filter, wherein the frame provides a substantially rigid material that is substantially resistant from ripping or tearing and is rigid and is able to maintain its integrity during and after undergoing a sterilization cycle. Exemplary configurations of the frame can be made out of polymer based materials or cellulose based materials. In other exemplary configurations, the frame is flexible and less rigid and may become deformed or shrink during a sterilization cycle. In another exemplary configuration, the frame can be made out of any type of material that is both flexible, less rigid and is able to maintain its integrity during and after undergoing a sterilization cycle. In one exemplary configuration, frame is composed of medical grade light board. In another exemplary configuration, frame is composed of a silicone material. The filter can be made of any type of porous paper or cellulose type material. In other configurations filter is made of polymeric substances, such as polypropylene. The filter is required to be porous enough to allow the passage of a sterilizing agent, such as steam through its membrane, but also resilient enough to not rip or tear during a sterilizing cycle. Exemplary configurations of the filter cartridge are able to provide sufficient integrity to form a sealed interface with a confronting surface, such as a sterilizing cabinet and/or a filter door or doors, and is able to maintain its integrity during and after undergoing a sterilization cycle.

Before the autoclave is opened by a user to remove the contents being sterilized, that is before the sterilized environment of the autoclave is exposed to the ambient environment, the interior of the sterilizing cabinet 100, 200, 300, 500 should have no more than a certain amount of moisture and a seal existing between any filter, or cartridge and the sterilizing cabinet. Thus, it is advantageous for a sterilizing cabinet 100, 200, 300, 500 to have only an amount of condensate that can be driven off or evaporated by the autoclave during a normal, or given or predetermined sterilizing cycle of the autoclave or during the post-sterilization cool down period.

Figure 9A:
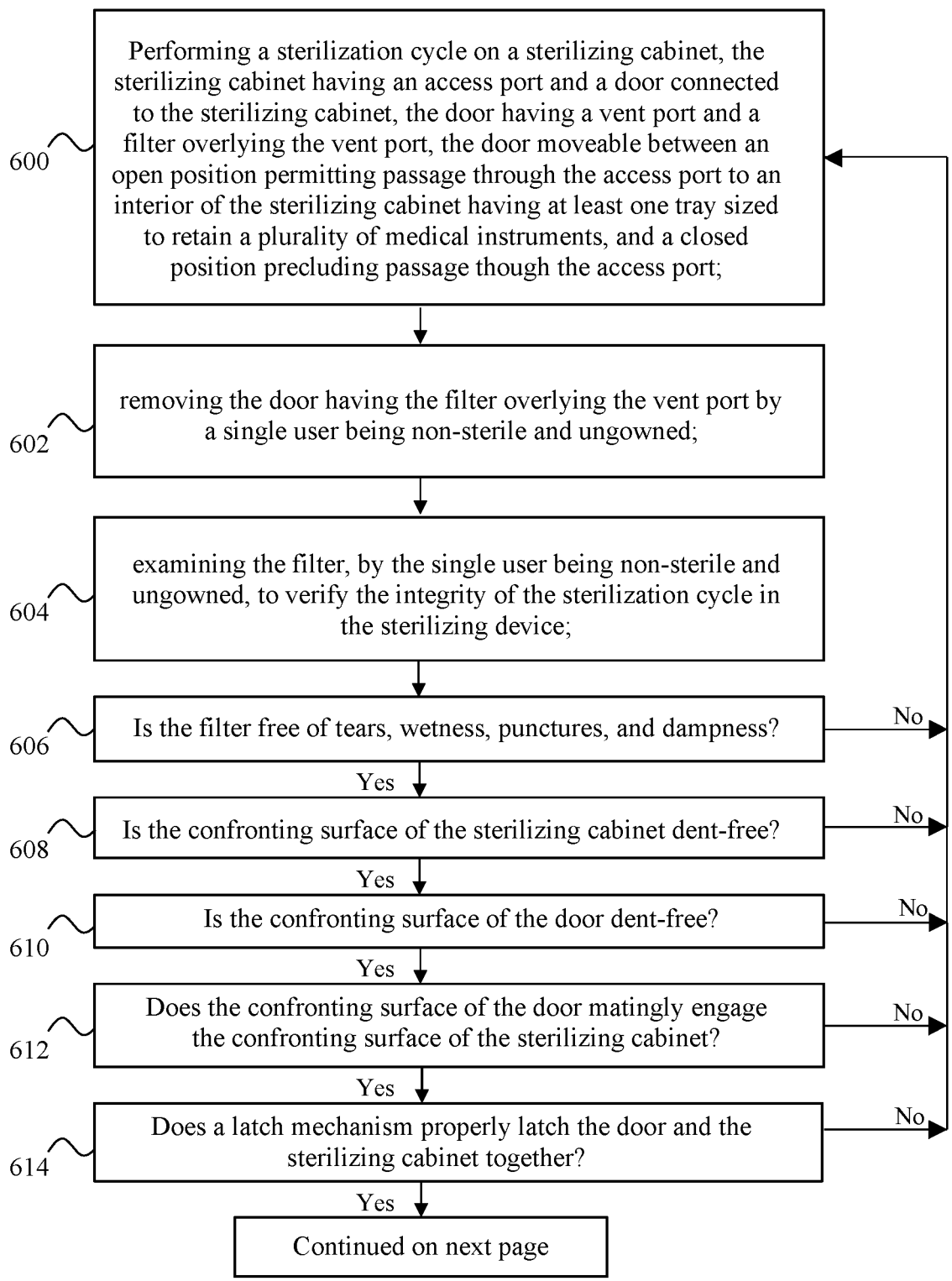
FIGS. 9A and 9B are a flow chart disclosing a method of sterilization verification in accordance with an exemplary configuration of the present disclosure.
Figure 9B:
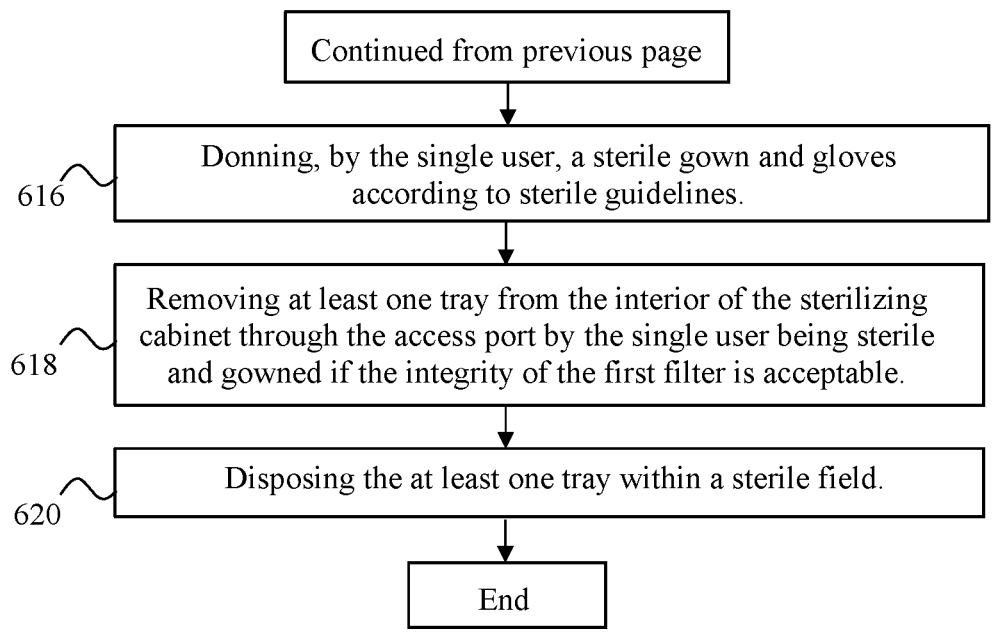

The following steps may be followed to verify sterilization of contents in a sterilizing cabinet 100, 200, or 300 as shown in FIGS. 9A and 9B. First, a sterilization cycle is performed on a sterilizing cabinet 100, 200, or 300 according to step 600. The sterilizing cabinet 100, 200, or 300 may include an access port and a door 106, 206, and/or 306 connected to the sterilizing cabinet 100, 200, 300. The door 106, 206, or 306 may further include a vent port 102, 234, or 312, and a filter 104, 210, 232, and/or 310 overlying the vent port 102, 234, and/or 312, wherein the door 106, 206 and/or 306 is moveable between an open position permitting passage through the access port and a closed position precluding passage through the access port. The sterilizing cabinet 100, 200, 300 contains items to be sterilized. The items to be sterilized may be medical instruments or other medical devices requiring sterilization as described supra. According to step 602, the door 106, 206, 306 is removed from the sterilizing cabinet 100, 200, 300 by a single user that has not yet followed sterile procedures and guidelines, including, but not limited to the Association of periOperative Registered Nurses (AORN)'s "Guideline for hand hygiene" and "Guideline for surgical attire," and is not yet gowned. The door 106, 206, or 306 may include the filter 104, 210, 232, 310 overlying the vent port 102, 234, 312. Where a sterilization cabinet includes a second door, for example as in sterilization cabinet 200, a user opens the first door 206 having a first filter 210 overlying vent port 202 and a second door 230 having a second filter 232, the second door including a vent port 234. The second door 230 may be removed by the user before removing the second filter 232 or the second door 230 and filter 232 may be removed together. In one configuration, the second door 230 is removed simultaneous with the first door 206 and in another configuration, the second door 230 is removed after the first door 206 and first filter 210 are removed. As the filter is accessible without removing any of the contents of the sterilizing cabinet 100, 200, 300, a single user that has not yet followed sterile procedures and guidelines for gowning and gloving, can inspect the filter or filters 104, 210, 232, 310 before following the sterile procedures and guidelines.

As set forth in step 604, the single user will examine the filter 104, 210, 232, 310 to verify the integrity of the sterilization cycle in the sterilizing device. At this point, the single user remains ungowned and has not yet followed sterile procedures and guidelines, including, but not limited to the Association of periOperative Registered Nurses (AORN)'s "Guideline for hand hygiene" and "Guideline for surgical attire," for gowning and gloving. According to step 606, the single user will determine if the filter(s) 104, 210, 232, and/or 310 is free of tears, punctures, wetness and dampness. If the filter(s) has a tear or puncture, or is wet or damp, the sterilization cycle must be repeated. The single user may replace the filter 104, 210, 232, 310 if it is torn or punctured or if the filter is a single-use filter. The single user then moves the door 106, 206, or 306 to the closed position precluding passage through the access port and repeats the sterilization cycle according to step 600. If two doors and/or two filters are selected, both sets of doors and/or filters are replaced before proceeding with the sterilization cycle of step 600. In this instance, the contents, for example, a plurality of trays, were never removed from the sterilizing cabinet 100, 200, 300, thereby (i) avoiding contaminating the "sterile field" area where the contents would have been placed; and (ii) avoiding an unnecessary step of re-gowning and gloving by the individual that removed the non-sterile contents from the sterilizing cabinet 100, 200, 300 due to the failure of the integrity of the sterilization cycle.

If the single user determines that the filter is free of tears, punctures, wetness and dampness, the single user may also determine any of the following steps: whether the confronting surface of the sterilizing cabinet is dent-free according to step 608, whether the confronting surface of the door is dent free according to step 610, whether the confronting surface of the door properly engages the confronting surface of the sterilizing cabinet as set forth in step 612, and whether the latch mechanism properly latches the door and the sterilizing cabinet of step 614. It should be appreciated that steps 608-614 may be performed by the user in any order. Moreover, although step 608 must be performed after each sterilization cycle, steps 610-614 are not required to be performed after each sterilization cycle. Thus, each of the steps 610-614 may be performed less frequently. If the single user determines that the sterilizing cabinet fails to conform to any of these steps 608-614, the non-conformity must be corrected and then the sterilizing cycle re-performed according to step 600. If the single user determines that all steps 606-614 are satisfied, then the single user, at this point, will follow the guidelines for sterile gowning and gloving to become sterile and gowned according to step 616. The user may, for example, follow the Association of periOperative Registered Nurses (AORN)'s "Guideline for hand hygiene" and "Guideline for surgical attire." Another medical professional may assist the user in drying, gowning, and gloving, but the additional medical professional is not needed for performance of the method steps set forth herein. At that point, the single user will remove the at least one tray from the interior of the sterilizing cabinet according to step 618 and dispose the at least one tray within a sterile field according to step 620 such that the sterility and integrity of the contents are maintained. The sterile field is prepared using aseptic practices. If the contents include an indicator that confirms proper sterilization, the user should inspect the indicator to confirm sterilization has been achieved, before placing the contents in the sterile field. In one configuration, the indicator is a tag or device that changes color when the sterilization is achieved.

Figure 10A:
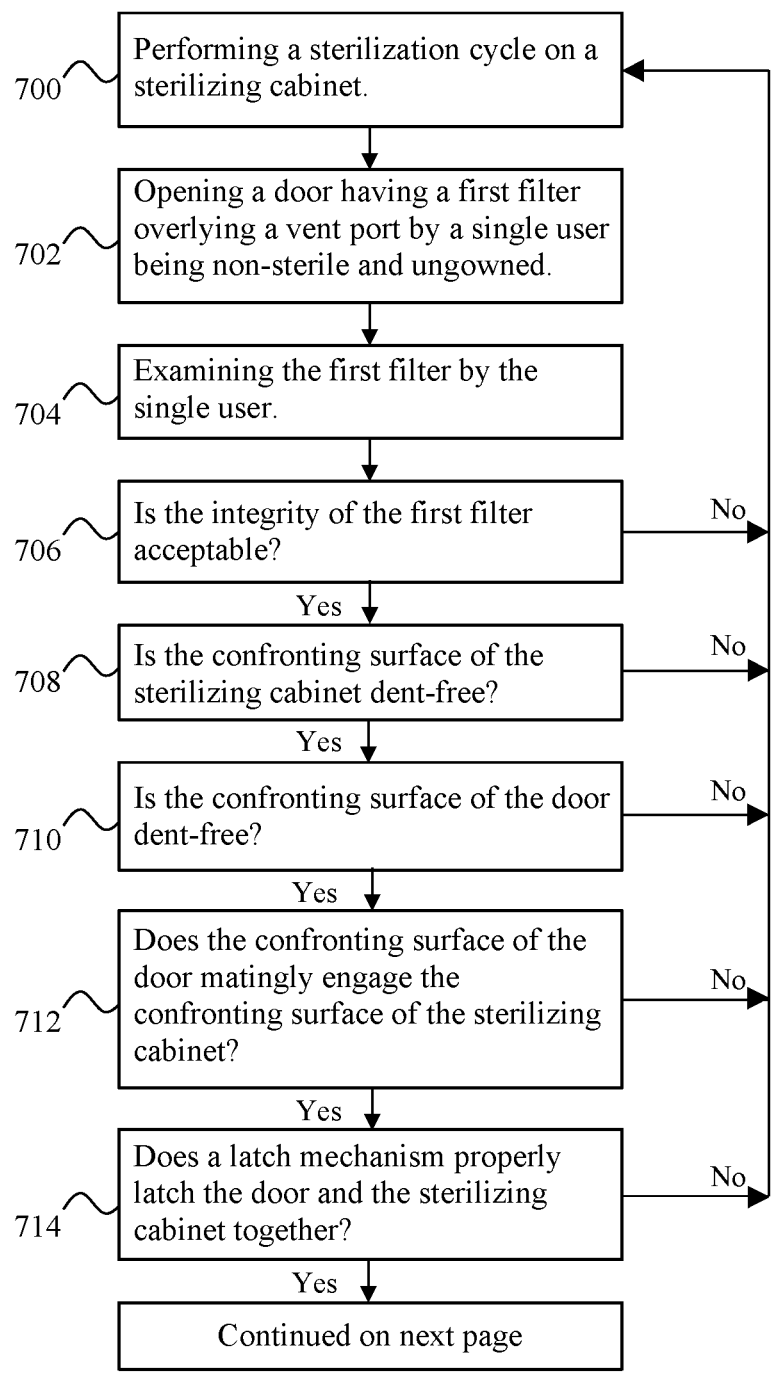
FIGS. 10A and 10B are a flow chart disclosing another example of a method of sterilization verification.
Figure 10B:
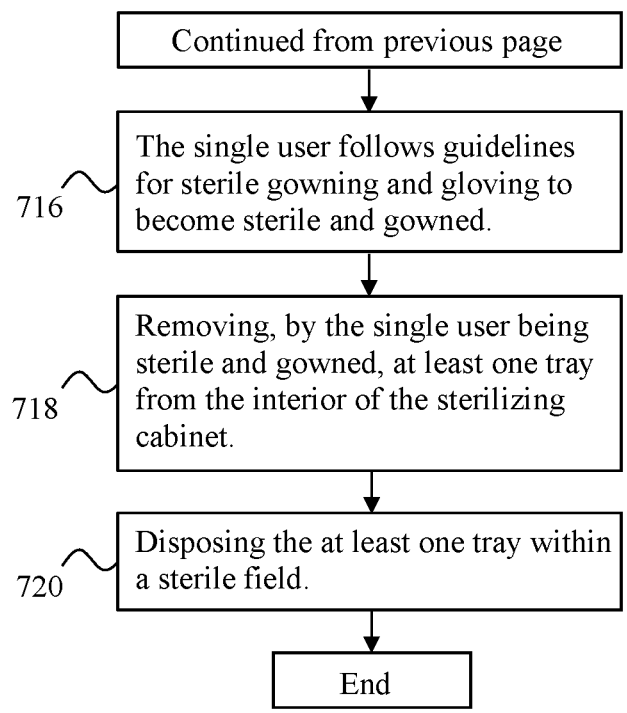

In yet another method of the present disclosure, a method of verifying the sterilization of contents in a sterilizing cabinet is shown in FIGS. 10A and 10B. First, a sterilization cycle may be performed on a sterilizing cabinet having contents to be sterilized according to step 700. In certain configurations, the sterilizing cabinet is sterilizing cabinet 100, 200, 300, or 500. Next, as set forth in step 702, a door, for example, door 106, 206, or 306, 550 and/or 552 is opened by a single user that is non-sterile and ungowned. In this configuration, the door 106, 206, 306, or 550 includes a first filter, for example, filter 104, 210, 310, or 508, which overlies a vent port, for example, vent port 102, 202, 234, 312, or 504. With respect to a configuration according to sterilizing cabinet 500, it should be appreciated that primary and secondary filter holders 550, 554 may be considered doors that overlie a vent port.

In the configuration where the door 106, 206, 306 is removeable, the door 106, 206, 306 and filter 104, 210, 310 may be removed together. In another configuration, the filter 104, 210, 310 may be removed separately from the door 106, 206, 306. In a configuration where the door 106, 206, 306, 550 and/or 552 is not removable from the sterilizing cabinet 100, 200, 300, 500, the door 106, 206, 306, 550 and/or 552 is opened and the filter 104, 210, 310, 508 and/or 510 is removed. Where the sterilization cabinet includes a second door, for example as in sterilization cabinet 200 and 500, a user first opens the first door 206, 552 having a first filter 210, 510 overlying vent port 202, 504 and, if desired, a second door 230, 550 having a second filter 232, 508. In certain configurations where the door is removeable, the second door 230 may be removed by the user before removing the second filter 232 or the second door 230 and filter 232 may be removed together. In one configuration, the second door 230 is removed simultaneous with the first door 206 and in another configuration, the second door 230 is removed after the first door 206 and first filter 210 are removed.

Next, according to step 704, the single user will examine the first filter considering whether the integrity of the first filter, for example, filter 104, 210, 310, and/or 510 is acceptable according to step 706, by determining whether the filter 104, 210, 310 and/or 510 has any holes, tears or punctures. Further, the single user will determine whether filter 104, 210, 310 and/or 510 is wet or damp. If the sterilizing cabinet 100, 200, 300, 500 includes more than one filter, the single user may also examine the additional filters to determine whether the filter includes any holes, tears, or punctures or is wet or damp. For example, the single user may also examine filter 234 or 508. The single user may also examine whether the confronting surface of the sterilizing cabinet is dent-free, according to step 708, whether the confronting surface of the door is dent-free according to step 710, and whether the confronting surface of the door matingly engages the confronting surface of the sterilizing cabinet according to step 712. If the sterilizing cabinet includes more than one door, the user will also examine the confronting surface(s) of the additional door(s) to confirm the surface(s) are dent free.

Further, the single user may determine whether the latch mechanism, if any, properly latches the door or doors and the sterilizing cabinet together according to step 714. If the user determines that the answer to any of steps 706 through 714 is "no," then the issue must be resolved and the sterilizing cycle repeated according to step 700. For example, if a confronting surface of the door or sterilizing cabinet is not dent free, the confronting surfaces of the sterilizing cabinet must be repaired before the sterilization cycle is repeated according to step 700. If the filters are torn, punctured, wet or damp the filter must be replaced and the sterilization cycle must be performed again on the contents of the sterilizing cabinet. In configurations where the filter is reuseable, a user may overlie the filter back over the vent port of the door instead of replacing the filter if the filter is wet or damp. Of course, if a filter is punctured or torn, it must be replaced before the sterilization cycle is repeated according to step 700. It should be appreciated that steps 706-714 may be performed by the user in any order. Moreover, although step 706 must be performed after each sterilization cycle, steps 708-714 are not required to be performed after each sterilization cycle. Thus, each of the steps 708-714 may be performed less frequently. If the user determines that the answer to each of the steps 706 through 714 is "yes," then the single user will then follow the guidelines for sterile gowning and gloving to become sterile and gowned according to step 716.

In one configuration, the sterile guidelines followed by the single user are the sterile guidelines approved by the Association of periOperative Registered Nurses (AORN) as set forth supra. At that point, the single user will remove the at least one tray from the interior of the sterilizing cabinet according to step 718 and dispose the tray within a sterile field according to step 720. The single user may continue to unload contents from the sterilizing cabinet until the contents of the sterilizing cabinet are fully removed. It should be appreciated that the single user may receive assistance in gowning and gloving from a sterile scrub person. However, the single user is the only person that is needed to verify the filter according to steps 706-714 and remove the tray from the interior of the sterilizing cabinet of step 718.

Thus, the present disclosure provides a method for verifying sterilization of contents within a sterilizing cabinet, wherein each step is performed by a single user.

What is claimed is:

1. A method for verifying sterilization, the method comprising:
performing a sterilization cycle on a sterilizing cabinet having an access port, an interior having at least one tray sized to retain a plurality of medical instruments, and a door having a vent port and a filter overlying the vent port, the door connected to the sterilizing cabinet and moveable between an open position permitting passage through the access port to an interior of the sterilizing cabinet and a closed position precluding passage through the access port;
opening the door with the first filter overlying the vent port by a single user being non-sterile and ungowned;
examining the first filter, by the single user being non-sterile and ungowned, to verify the integrity of the sterilization cycle in the sterilizing device;
determining if the integrity of the first filter is acceptable by the single user being non-sterile and ungowned;
removing, by the single user being sterile and gowned, through the access port at least one tray from the interior of the sterilizing cabinet if the integrity of the first filter is acceptable.

2. The method for verifying sterilization of claim 1, further comprising the step of disposing the at least one tray within a sterile field.

3. The method for verifying sterilization of claim 1, wherein the door is a filter holder moveable between an open position and a closed position and configured to hold the first filter overlying the vent port and a second filter overlying at least a portion of the first filter.

4. The method for verifying sterilization of claim 1, further comprising the step of following, by the single user, guidelines for sterile gowning and gloving to become sterile and gowned.

5. The method for verifying sterilization of claim 4, wherein the guidelines for sterile gowning and gloving are the sterile guidelines approved by the Association of periOperative Registered Nurses (AORN).

6. The method for verifying sterilization of claim 4, wherein the step of following, by the single user, guidelines for sterile gowning and gloving, includes the step of receiving assistance in gowning and gloving from a sterile scrub person.

7. The method for verifying sterilization of claim 1, further comprising, before the step of removing, by the single user being sterile and gowned, through the access port at least one tray, the step of:
confirming a confronting surface of the sterilizing cabinet and a confronting surface of the door are dent-free;
confirming the confronting surface of the door matingly engages the confronting surface of the sterilizing cabinet; and,
confirming a latch mechanism properly latches the door and the sterilizing cabinet together.

8. The method for verifying sterilization of claim 7, wherein the step of opening the door includes breaking a sealed interface between the confronting surface of the sterilizing cabinet and the confronting surface of the door.

9. The method for verifying sterilization of claim 1, wherein the at least one tray sized to retain a plurality of medical instruments is an unwrapped tray.

10. The method for verifying sterilization of claim 1, wherein a plurality of trays sized to retain a plurality of medical instruments are removed through the access port by the single user being sterile and gowned.

11. The method for verifying sterilization of claim 1, wherein the integrity of the filter is determined to be acceptable if the filter is free of tears, wetness, punctures, and dampness.

12. A method for verifying sterilization, the method comprising:
performing a sterilization cycle on a sterilizing cabinet, the sterilizing cabinet having an access port and a door connected to the sterilizing cabinet, the door having a vent port and a filter overlying the vent port, the door moveable between an open position permitting passage through the access port to an interior of the sterilizing cabinet having at least one tray sized to retain a plurality of medical instruments, and a closed position precluding passage though the access port;
removing the door having the filter overlying the vent port by a single user being non-sterile and ungowned;
examining the filter, by the single user being non-sterile and ungowned, to verify the integrity of the sterilization cycle in the sterilizing device;
determining whether the integrity of the filter is acceptable by the single user being non-sterile and ungowned; and
removing at least one tray from the interior of the sterilizing cabinet through the access port by the single user being sterile and gowned if the integrity of the first filter is acceptable.

13. The method for verifying sterilization of claim 12, wherein the single user being sterile and gowned includes the step of donning, by the single user, a sterile gown and gloves according to sterile guidelines.

14. The method for verifying sterilization of claim 13, wherein the sterile guidelines are the gowning and gloving are the sterile guidelines approved by the Association of periOperative Registered Nurses (AORN).

15. The method for verifying sterilization of claim 13, wherein the step of donning, by the single user, a sterile gown and gloves includes the step of receiving, by the single user, assistance in gowning and gloving from a sterile scrub person.

16. The method for verifying sterilization of claim 12, wherein the integrity of the filter is determined to be acceptable if the filter is free of tears, wetness, punctures, and dampness.

17. The method for verifying sterilization of claim 12, wherein the sterilizing cabinet contains a plurality of trays, each sized to retain a plurality of medical instruments, the method further comprising the step of disposing the plurality of trays within a sterile field.

18. The method for verifying sterilization of claim 12, further comprising, before the step of removing at least one tray from the interior of the sterilizing cabinet through the access port by the single user being sterile and gowned, the steps of:
confirming a confronting surface of the sterilizing cabinet and a confronting surface of the door are dent-free;
confirming the confronting surface of the door matingly engages the confronting surface of the sterilizing cabinet; and,
confirming a latch mechanism properly latches the door and the sterilizing cabinet together.

19. The method for verifying sterilization of claim 12, wherein the at least one tray sized to retain a plurality of medical instruments is an unwrapped tray.

* * * * *